United States Patent
Taniike et al.

(10) Patent No.: US 6,599,407 B2
(45) Date of Patent: *Jul. 29, 2003

(54) BIOSENSOR

(75) Inventors: Yuko Taniike, Osaka (JP); Shin Ikeda, Katano (JP); Shiro Nankai, Hirakata (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/747,975

(22) Filed: Dec. 27, 2000

(65) Prior Publication Data

US 2001/0006149 A1 Jul. 5, 2001

(30) Foreign Application Priority Data

Dec. 27, 1999 (JP) .......................................... 11-369836

(51) Int. Cl.⁷ ............................................ G01N 27/327
(52) U.S. Cl. .............................. 204/403.1; 204/403.14; 204/403.01
(58) Field of Search ..................... 204/403, 403.01, 204/403.04, 403.09, 403.1, 403.11, 403.14

(56) References Cited

U.S. PATENT DOCUMENTS 4,545,382 A    10/1985  Higgins et al. ............. 600/347
5,378,332 A     1/1995  Pandey ..................... 205/777.5
6,129,823 A  * 10/2000  Hughes et al. .............. 204/409

FOREIGN PATENT DOCUMENTS

| EP | 0636879 | 2/1995 |
| EP | 0 901 018 | 3/1999 |
| EP | 0901018 | 3/1999 |
| EP | 0965301 | 12/1999 |
| JP | 3-202764 | 9/1991 |
| WO | WO 92/07263 | 4/1992 |

* cited by examiner

Primary Examiner—Jill Warden
Assistant Examiner—Alex Noguerola
(74) Attorney, Agent, or Firm—McDermott, Will & Emery

(57) ABSTRACT

The present invention provides a biosensor having a favorable response characteristic up to a high concentration range, a low blank response and a high storage stability. This sensor comprises an electrode system including a working electrode and a counter electrode, for forming an electrochemical measurement system by coming in contact with a supplied solution; an electrically insulating supporting member for supporting the electrode system; a first reagent layer formed on the working electrode; and a second reagent layer formed on the counter electrode, wherein the first reagent layer comprises an enzyme as the main component, and the second reagent layer comprises an electron mediator as the main component.

5 Claims, 7 Drawing Sheets

BIOSENSOR

BACKGROUND OF THE INVENTION

The present invention relates to a biosensor for rapid quantification of a substrate contained in a sample with high accuracy.

Conventionally, methods using polarimetry, colorimetry, reductimetry and a variety of chromatography have been developed as the measure for quantitative analysis of sugars such as sucrose and glucose. However, those conventional methods are all poorly specific to sugars and hence have poor accuracy. Among them, the polarimetry is simple in manipulation, but it is largely affected by the temperature during the manipulation. Therefore, this method is not suitable for simple quantification of sugars at home by ordinary people.

In recent years, a variety of biosensors have been developed which best utilize a specific catalytic action of enzymes.

In the following, a method of quantitative analysis of glucose will be explained as an example of the method for quantifying a substrate contained in a sample. Conventionally known electrochemical quantification of glucose includes a method using a combination of glucose oxidase (EC 1.1.3.4: hereinafter abbreviated to "GOD") as an enzyme with an oxygen electrode or a hydrogen peroxide electrode (see "Biosensor" ed. by Shuichi Suzuki, Kodansha, for example).

GOD selectively oxidizes β-D-glucose as a substrate to D-glucono-δ-lactone using oxygen as an electron mediator. Oxygen is reduced to hydrogen peroxide during the oxidation reaction by GOD in the presence of oxygen. A decreased volume of oxygen is measured by the oxygen electrode, or an increased volume of hydrogen peroxide is measured by the hydrogen peroxide electrode. The decreased volume of oxygen or, otherwise, the increased volume of hydrogen peroxide is proportional to the content of glucose in the sample. It is therefore possible to quantify glucose based on the decreased volume of oxygen or the increased volume of hydrogen peroxide.

In the above method, it is possible to quantify glucose in the sample accurately by using the specificity of the enzyme reaction. However, as speculated from the reaction, this prior art method has a drawback that the measurement result is greatly affected by the oxygen concentration in the sample. Hence, in the event where oxygen is absent in the sample, measurement is infeasible.

Under such a circumstance, a glucose sensor of new type has been developed which uses as the electron mediator an organic compound or a metal complex such as potassium ferricyanide, a ferrocene derivative and a quinone derivative, in place of oxygen in the sample. The sensor of this type oxidizes the reduced electron mediator resulting from the enzyme reaction on a working electrode so as to determine the glucose concentration in the sample based on an oxidation current produced by the oxidation reaction. At this time, on a counter electrode, the oxidized electron mediator is reduced, and a reaction for generating the reduced electron mediator proceeds. With the use of such an organic compound or metal complex as the electron mediator in place of oxygen, it is possible to form a reagent layer by precisely placing a known amount of GOD together with the electron mediator in their stable state on the electrode, thereby enabling accurate quantification of glucose without being affected by the oxygen concentration in the sample. In this case, it is also possible to integrate the reagent layer containing the enzyme and electron mediator with an electrode system while keeping the reagent layer in an almost dry state, and therefore a disposable glucose sensor based on this technology has recently been noted considerably. A typical example of such a glucose sensor is a biosensor disclosed in Japanese Laid-Open Patent Publication Hei 3-202764. With such a disposable glucose sensor, it is possible to measure the glucose concentration easily with a measurement device by simply introducing a sample into the sensor connected detachably to the measurement device. The application of such a technique is not limited to quantification of glucose and may be extended to quantification of any other substrate contained in the sample.

However, in the above-described conventional biosensors, when the sample contains a substrate at high concentrations, the enzyme reaction proceeds also on the counter electrode and supply of the electron mediator to the counter electrode thus becomes insufficient, so that the reaction at the counter electrode becomes a rate determining step, which makes it impossible to obtain a current response proportional to the substrate concentration. Therefore, such biosensors have a problem that quantification of a substrate is not possible when the sample contains a substrate at high concentrations.

In recent years, there is a demand for a biosensor exhibiting a low response when the substrate concentration is zero and excellent storage stability. The response obtained when the substrate concentration is zero is hereinafter referred to as "blank response".

BRIEF SUMMARY OF THE INVENTION

The present invention provides a biosensor comprising: an electrode system including a working electrode and a counter electrode, for forming an electrochemical measurement system by coming in contact with a supplied sample solution; an electrically insulating supporting member for supporting the electrode system; a first reagent layer formed on the working electrode; and a second reagent layer formed on the counter electrode, wherein the first reagent layer comprises an enzyme as the main component, and the second reagent layer comprises an electron mediator as the main component.

It is preferred that the first reagent layer does not contain an electron mediator and that the second reagent layer does not contain an enzyme.

In a preferred mode of the present invention, the supporting member comprises an electrically insulating base plate on which the working electrode and the counter electrode are formed.

In another preferred mode of the present invention, the supporting member comprises an electrically insulating base plate and an electrically insulating cover member for forming a sample solution supply pathway or a sample solution storage section between the cover member and the base plate, the working electrode is formed on the base plate, and the counter electrode is formed on an inner surface of the cover member so as to face the working electrode.

It is preferred that the cover member comprises a sheet member having an outwardly expanded curved section, for forming a sample solution supply pathway or a sample solution storage section between the cover member and the base plate.

In a more preferred mode of the present invention, the cover member comprises a spacer having a slit for forming the sample solution supply pathway and a cover for covering the spacer.

It is preferred that at least the first reagent layer contains a hydrophilic polymer.

While the novel features of the invention are set forth particularly in the appended claims, the invention, both as to organization and content, will be better understood and appreciated, along with other objects and features thereof, from the following detailed description taken in conjunction with the drawings.

DETAILED DESCRIPTION OF THE INVENTION

Figure 1:
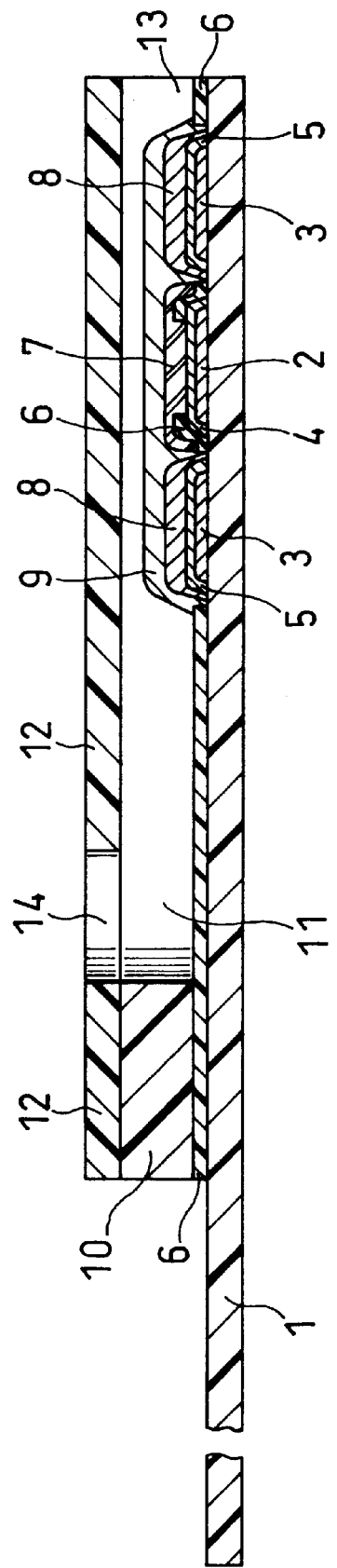
FIG. 1 is a vertical cross-sectional view of a glucose sensor according to one example of the present invention.

A biosensor in accordance with a preferred mode of the present invention comprises an electrically insulating base plate; a working electrode and a counter electrode formed on the base plate; a first reagent layer formed on the working electrode; and a second reagent layer formed on the counter electrode, wherein the first reagent layer comprises an enzyme as the main component, and the second reagent layer comprises an electron mediator as the main component.

In this biosensor, the enzyme reaction hardly proceeds at the counter electrode especially when the sample contains a substrate at high concentrations, since the main component of the second reagent layer on the counter electrode is the electron mediator. Thus, the probability of collision between the enzyme and the electron mediator decreases in the sample solution in which the reagents are dissolved, so that the linearity of response current is decreased. However, since sufficient electron mediator is retained on the counter electrode for the reaction, the reaction at the counter electrode does not become a rate determining step. As a result, the linearity of response current can be maintained even up to a high substrate-concentration range.

A biosensor in accordance with another preferred mode of the present invention comprises an electrically insulating base plate; an electrically insulating cover member for forming a sample solution supply pathway or a sample solution storage section between the cover member and the base plate; a working electrode formed on the base plate; a counter electrode formed on an inner surface of the cover member so as to face the working electrode; a first reagent layer formed on the working electrode; and a second reagent layer formed on the counter electrode.

The cover member comprises a sheet member having an outwardly expanded curved section, for forming a sample solution supply pathway or a sample solution storage section between the cover member and the base plate.

A more preferred cover member comprises a spacer with a slit for forming the sample solution supply pathway and a cover for covering the spacer.

In such a biosensor, since the first reagent layer and second reagent layer are formed on separate members, respectively, the first reagent layer and second reagent layer having different compositions can be readily separated from each other. Moreover, since the working electrode and counter electrode are formed at opposite positions, the ion tranfer between the electrodes is facilitated, thereby further increasing the current response.

In a biosensor whose cover member comprises the spacer and cover, since the physical strength of the cover is enhanced, the first reagent layer and second reagent layer are not brought into contact with each other by an external physical pressure, thereby preventing degradation in the enzyme activity due to the contact between the enzyme and the electron mediator.

In either of the biosensors of the above-described embodiments, it is preferred that at least the first reagent layer contains a hydrophilic polymer. Since the hydrophilic polymer prevents adsorption of proteins, etc. to the working electrode, the current response sensitivity is further improved. Besides, during the measurement, since the viscosity of a sample solution is increased by the hydrophilic polymer dissolved in the sample solution, the effects of physical impact, etc. on the current response are reduced, thereby improving the stability of the current response.

In the present invention, for the base plate, spacer and cover, it is possible to use any material having an insulating property and sufficient rigidity during storage and measurement. Examples of such a material include thermoplastic resins such as polyethylene, polystyrene, polyvinyl chloride, polyamide and saturated polyester resin, or thermosetting resins such as a urea resin, melamine resin, phenol resin, epoxy resin and unsaturated polyester resin. Among these resins, polyethylene terephthalate is preferred in view of the adhesiveness to the electrode.

For the working electrode, it is possible to use any conductive material if it is not oxidized itself in oxidizing the electron mediator. For the counter electrode, it is possible to use a generally used conductive material such as palladium, silver, platinum, and carbon.

As the enzyme, it is possible to use the one suitable for the type of a substrate in the sample, which is the subject of measurement. Examples of the enzyme include fructose dehydrogenase, glucose oxidase, alcohol oxidase, lactate oxidase, cholesterol oxidase, xanthine oxidase, and amino acid oxidase.

Examples of the electron mediator include potassium ferricyanide, p-benzoquinone, phenazine methosulfate, methylene blue, and ferrocene derivatives. Besides, even when oxygen is used as the electron mediator, a current response is obtained. These electron mediators are used singly or in combinations of two or more.

A variety of hydrophilic polymers are applicable. Examples of the hydrophilic polymer include hydroxyethyl cellulose, hydroxypropyl cellulose, methyl cellulose, ethyl cellulose, ethylhydroxyethyl cellulose, carboxymethyl cellulose, polyvinyl pyrrolidone, polyvinyl alcohol, polyamino acid such as polylysine, polystyrene sulfonate, gelatin and its derivatives, polyacrylic acid and its salts, plolymethacrylic acid and its salts, starch and its derivatives, and a polymer of maleic anhydride or a maleate. Among them, carboxymethyl cellulose, hydroxyethyl cellulose and hydroxypropyl cellulose are particularly preferred.

The following description will explain the present invention in further detail by illustrating examples thereof.

EXAMPLE 1

A glucose sensor will be explained as an example of a biosensor.

Figure 2:
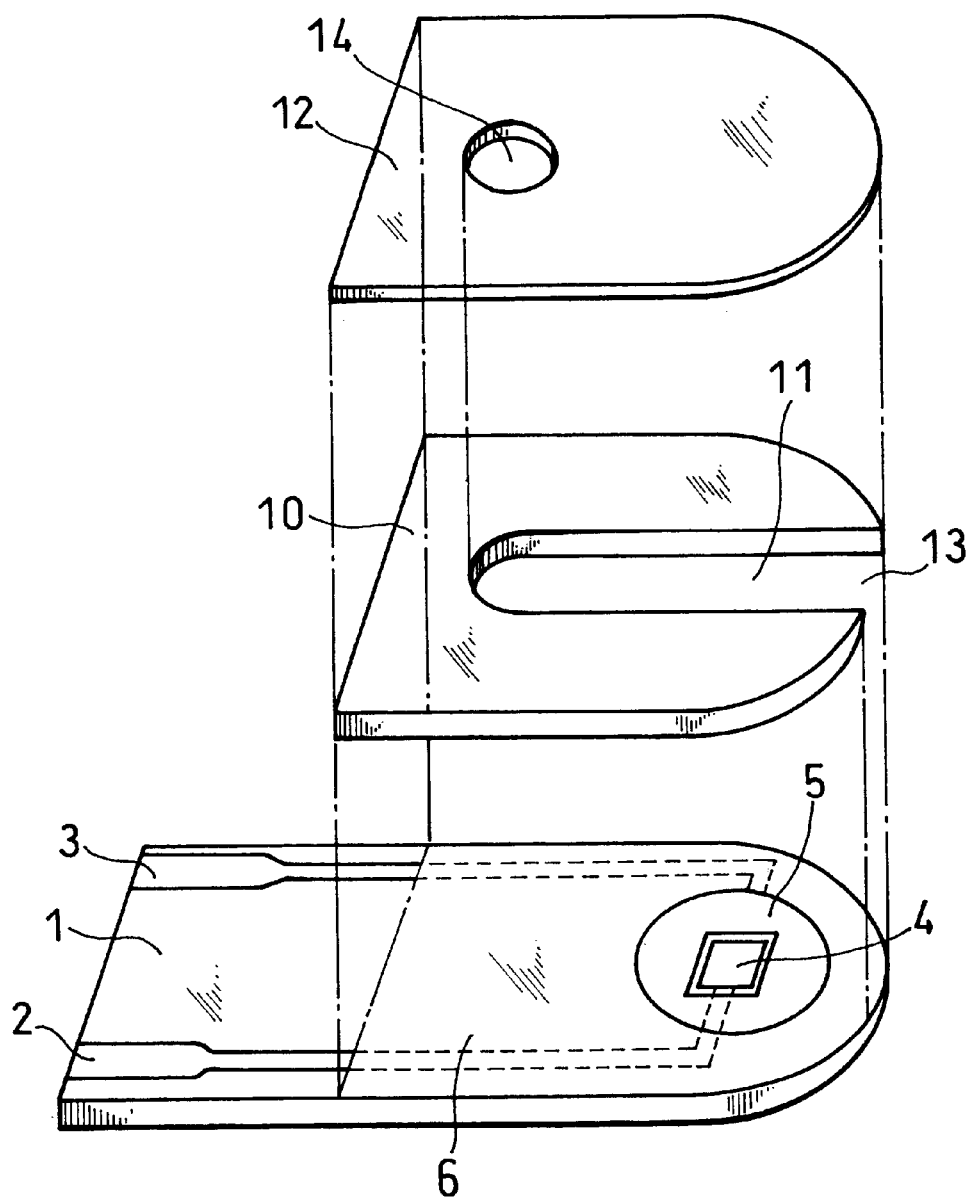
FIG. 2 is an exploded perspective view of the glucose sensor, omitting the reagent layers and surface active agent layer therefrom.

FIG. 1 is a vertical cross-sectional view of a glucose sensor of this example, and FIG. 2 is an exploded perspective view of the glucose sensor, omitting the reagent layers and surface active agent layer therefrom.

First, a silver paste was printed on an electrically insulating base plate 1 made of polyethylene terephthalate by screen printing to form leads 2 and 3 and the base of later-described electrodes. Then, a conductive carbon paste containing a resin binder was printed on the base plate 1 to form a working electrode 4. This working electrode 4 was in contact with the lead 2. Further, an insulating paste was printed on the base plate 1 to form an insulating layer 6. The insulating layer 6 covered the peripheral portion of the working electrode 4 so that a fixed area of the working electrode 4 was exposed. Next, a counter electrode 5 was formed by printing a conductive carbon paste containing a resin binder so as to be in contact with the lead 3.

A first aqueous solution containing GOD as an enzyme and no electron mediator was dropped on the working electrode 4 of the base plate 1 and then dried to form a first reagent layer 7. Besides, a second aqueous solution containing potassium ferricyanide as an electron mediator and no enzyme was dropped on the counter electrode 5 of the base plate 1 and then dried to form a second reagent layer 8. Further, in order to achieve smooth supply of a sample, a layer 9 containing lecithin as a surface active agent was formed so as to cover the first reagent layer 7 and the second reagent layer 8.

Finally, the base plate 1, a cover 12 and a spacer 10 were adhered to each other in a positional relationship as shown by the dashed lines in FIG. 2 to fabricate the glucose sensor.

The spacer 10 to be inserted between the base plate 1 and the cover 12 has a slit 11 for forming a sample solution supply pathway between the base plate 1 and the cover 12.

Since an air vent 14 of the cover 12 communicates with this sample solution supply pathway, when the sample is brought into contact with a sample supply port 13 formed at an open end of the slit 11, the sample readily reaches the first reagent layer 7 and second reagent layer 8 in the sample solution supply pathway because of capillary phenomenon.

Figure 7:
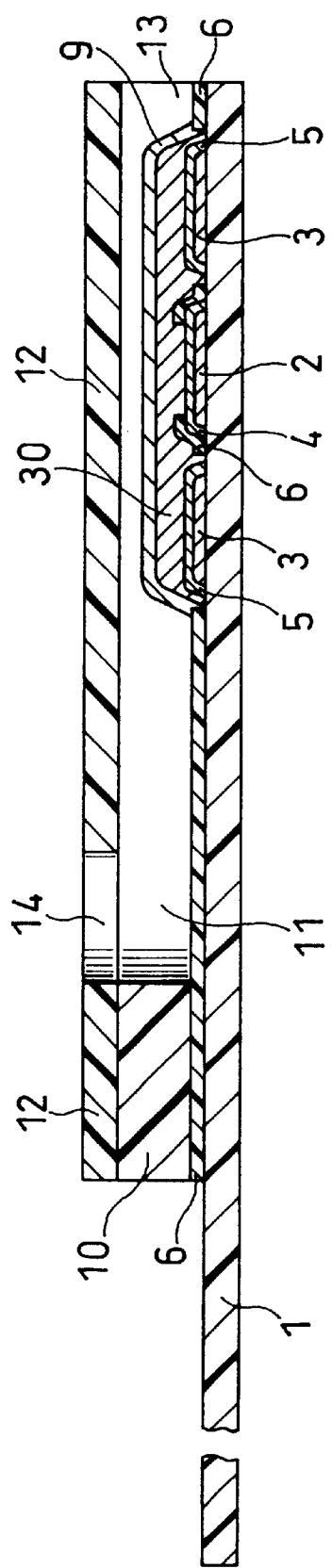
FIG. 7 is a vertical cross-sectional view of a glucose sensor of a comparative example.

As a comparative example, a glucose sensor was fabricated in the same manner as this example with the exception of the process of forming the reagent layers. FIG. 7 is a vertical cross-sectional view of the glucose sensor of the comparative example. A reagent layer 30 was formed by dropping an aqueous solution containing GOD and potassium ferricyanide on the working electrode 4 and counter electrode 5 and then drying the aqueous solution. Moreover, a layer 9 containing lecithin as a surface active agent was formed on the reagent layer 30.

Next, with the glucose sensors of Example 1 and the comparative example, the concentration of glucose was measured using a solution containing a certain amount of glucose as a sample. The sample was supplied to the sample solution supply pathway from the sample supply port 13 and, after elapse of a certain time, a voltage of 500 mV was applied to the working electrode 4 using the counter electrode 5 as reference. Since the spacer 10 is interposed between the cover 12 and the base plate 1, the strength of the sensor against an external physical pressure is increased. Consequently, the volume of the sample solution supply pathway is readily kept constant, and the effects of physical pressure, etc. on the current response are reduced.

The value of a current which flowed across the working electrode 4 and the counter electrode 5 upon the application of this voltage was measured. As a result, in both of Example 1 and the comparative example, a current response proportional to the glucose concentration in the sample was observed. When the sample comes into contact with the first reagent layer 7 and the second reagent layer 8, potassium ferricyanide as the oxidized form of the electron mediator dissociates into ferricyanide ion and potassium ion. The glucose in the sample, the ferricyanide ion dissolved in the sample from the second reagent layer 8 and the GOD react with each other. As a result, the glucose is oxidized into glucono lactone, and the oxidized form ferricyanide ion is reduced to the reduced form ferrocyanide ion. A reaction of oxidizing ferrocyanide ion into ferricyanide ion proceeds on the working electrode 4, while a reaction of reducing ferricyanide ion into ferrocyanide ion proceeds on the counter electrode 5. Since the concentration of ferrocyanide ion is proportional to the concentration of glucose, it is possible to measure the concentration of glucose based on the oxidation current of the ferrocyanide ion.

In the glucose sensor of this example, high linearity was observed up to a higher glucose concentration than in the glucose sensor of the comparative example for the following reasons.

Since GOD and potassium ferricyanide are separately carried on the working electrode and the counter electrode, respectively, the enzyme reaction hardly proceeds at the counter electrode. Thus, sufficient concentration of potassium ferricyanide is retained on the counter electrode, preventing the reaction at the counter electrode from becoming a rate determining step even when the sample contains a substrate at high concentrations. As a result, it is possible to maintain the linearity of response current up to a high concentration range. In the sensor of the comparative example, on the other hand, the enzyme reaction proceeds on the counter electrode to the extent which is almost equivalent to that on the working electrode, causing reduction of ferricyanide ion into ferrocyanide ion. Consequently, the ferricyanide ion becomes insufficient for the reaction on the counter electrode, so that the reaction at the counter electrode becomes a rate determining step.

Further, in the glucose sensor of this example, the blank response was lowered and the current response was not changed so much even after a long-time storage in comparison with the glucose sensor of the comparative example. This is because GOD and potassium ferricyanide were separated from each other so that it was possible to prevent contact and interaction between GOD and potassium ferricyanide, thereby suppressing an increase in the blank response and degradation in the enzyme activity during a long-time storage.

EXAMPLE 2

Figure 3:
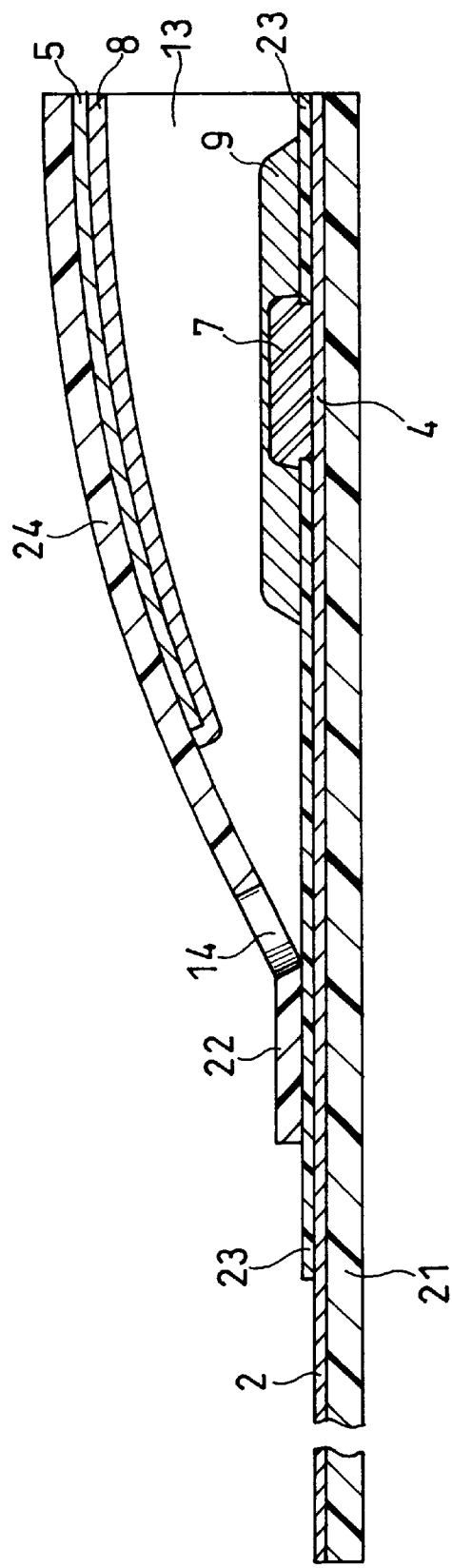
FIG. 3 is a vertical cross-sectional view of a glucose sensor according to another example of the present invention.
Figure 4:
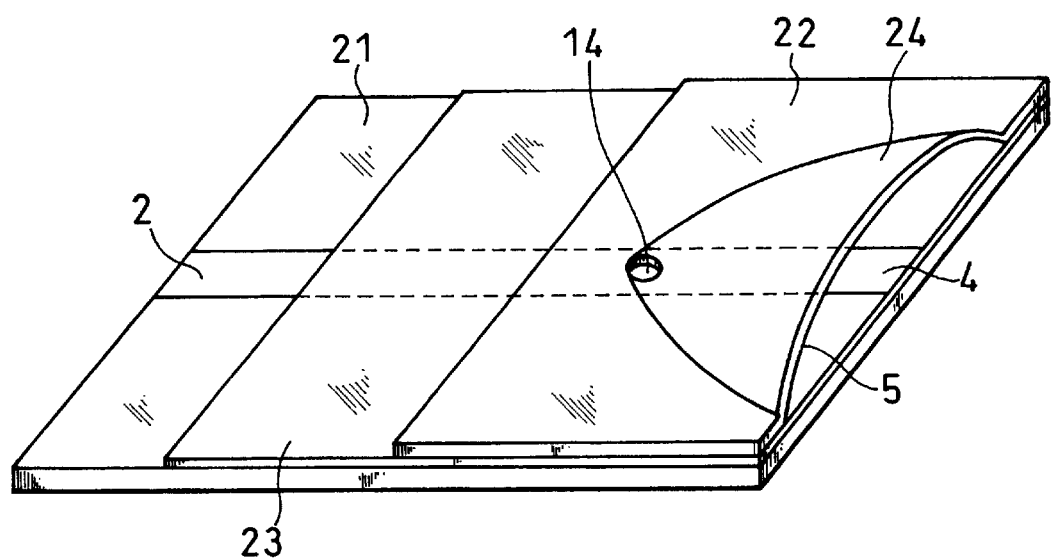
FIG. 4 is an exploded perspective view of the glucose sensor, omitting the reagent layers and surface active agent layer therefrom.

FIG. 3 is a vertical cross-sectional view of a glucose sensor of this example, and FIG. 4 is an exploded perspective view of the glucose sensor, omitting the reagent layers and surface active agent layer therefrom.

A working electrode 4 and a lead 2 were formed by sputtering palladium on an electrically insulating base plate 21. Next, by pasting an insulating sheet 23 on the base plate 21, the working electrode 4 and a terminal section to be inserted into a measurement device were defined.

Meanwhile, a counter electrode 5 was formed by sputtering palladium onto the inner wall surface of an outwardly expanded curved section 24 of an electrically insulating cover member 22. An end portion of the curved section 24 was provided with an air vent 14.

A first aqueous solution containing GOD as an enzyme and no electron mediator was dropped on the working electrode 4 of the base plate 21 and then dried to form a first reagent layer 7. Besides, a second aqueous solution containing potassium ferricyanide as an electron mediator and no enzyme was dropped on the counter electrode 5 of the cover member 22 to form a second reagent layer 8. Further, a layer 9 containing lecithin as a surface active agent was formed on the first reagent layer 7.

Finally, the base plate 21 and cover 22 were adhered to each other to fabricate the glucose sensor. Accordingly, the working electrode 4 and the counter electrode 5 are positioned to face each other with a space formed between the base plate 21 and the curved section 24 of the cover member 22 therebetween. This space serves as a sample storage section and, when a sample is brought into contact with an open end of the space, the sample readily moves toward the air vent 14 due to capillary phenomenon and comes into contact with the first reagent layer 7 and second reagent layer 8.

Next, the concentration of glucose was measured according to the same procedure as in Example 1. As a result, a current response proportional to the concentration of glucose in the sample was observed. The counter electrode 5 was electrically connected by holding an end portion of the curved section 24 with a clip connected to a lead wire.

In the glucose sensor of Example 2, the second reagent layer 8 contained only potassium ferricyanide, so that high linearity was observed up to a higher glucose concentration than in the glucose sensor of the comparative example, like Example 1. Also, in this biosensor, like Example 1, the blank response was lowered, and the current response was not changed so much even after a long-time storage in comparison with the comparative example, since GOD and potassium ferricyanide were separated from each other. Further, in comparison with the comparative example, an increase in the response value was observed, because the working electrode 4 and counter electrode 5 were formed at opposite positions so that ion transfer between the electrodes was facilitated.

EXAMPLE 3

Figure 5:
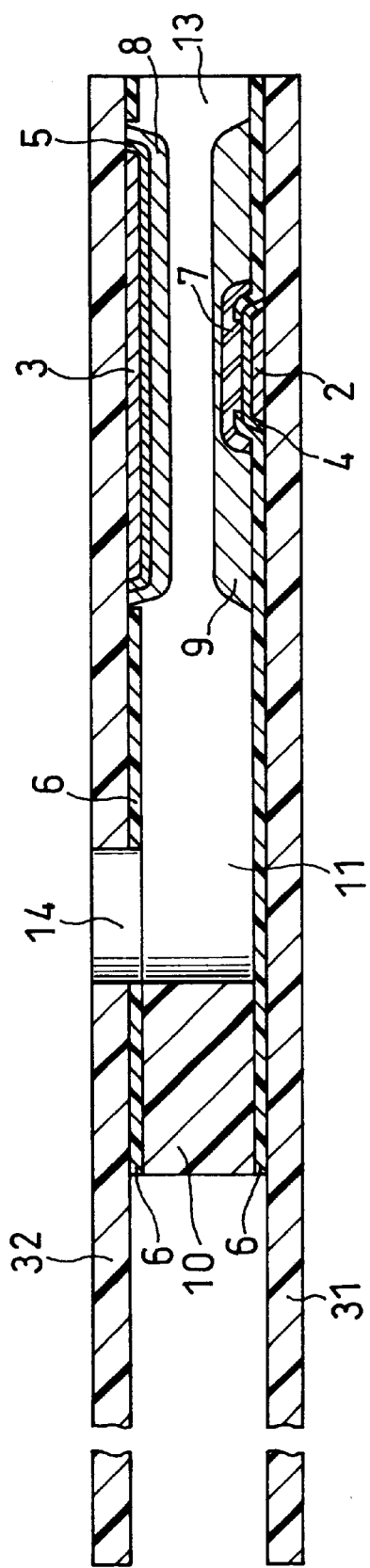
FIG. 5 is a vertical cross-sectional view of a glucose sensor according to still another example of the present invention.
Figure 6:
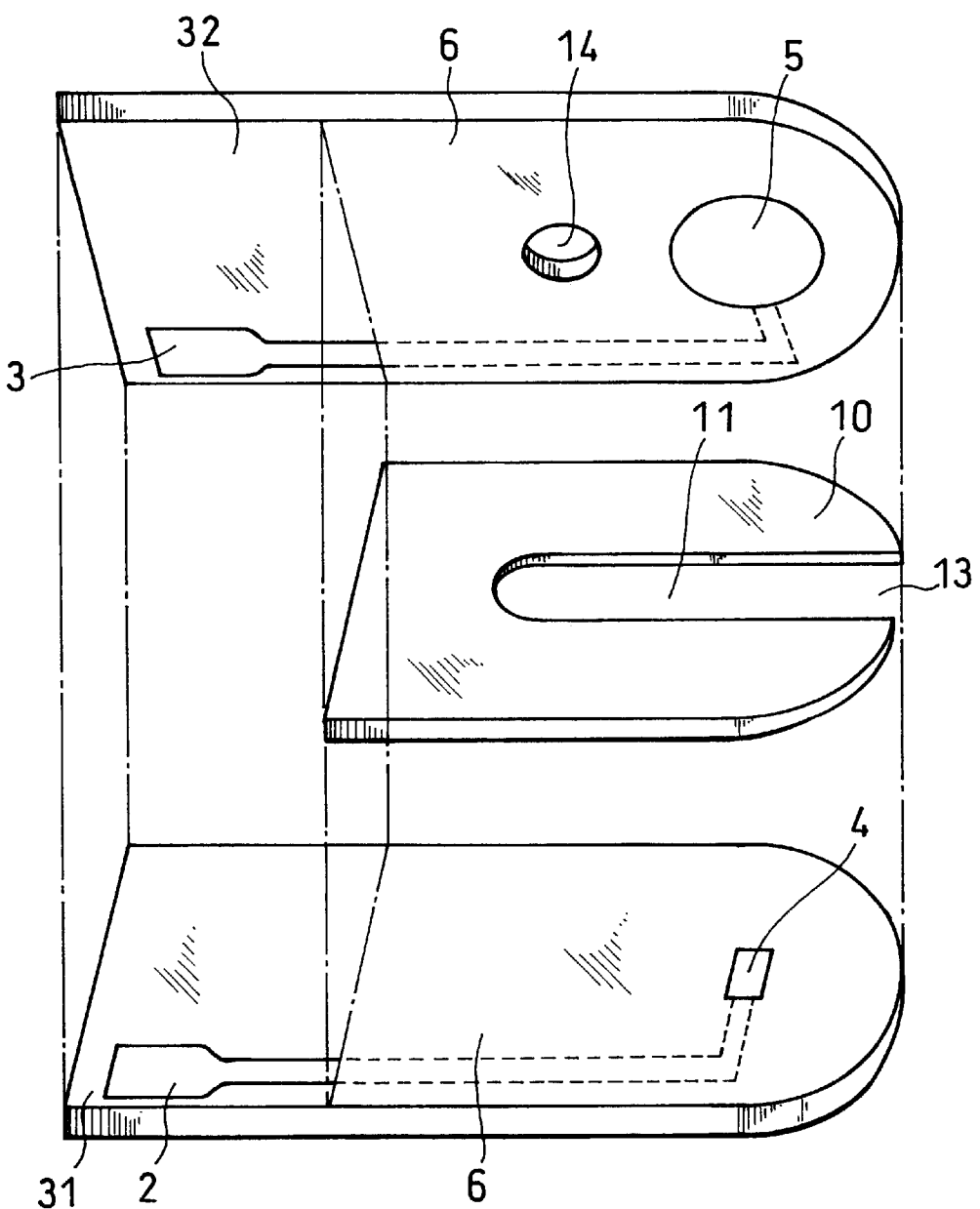
FIG. 6 is an exploded perspective view of the glucose sensor, omitting the reagent layers and surface active agent layer therefrom.

FIG. 5 is a vertical cross-sectional view of a glucose sensor of this example, and FIG. 6 is an exploded perspective view of the glucose sensor, omitting the reagent layers and surface active agent layer therefrom.

First, a silver paste was printed on an electrically insulating base plate 31 made of polyethylene terephthalate by screen printing to form a lead 2. Then, a conductive carbon paste containing a resin binder was printed on the base plate 31 to form a working electrode 4. This working electrode 4 was in contact with the lead 2. Further, an insulating paste was printed on the base plate 31 to form an insulating layer 6. The insulating layer 6 covered the peripheral portion of the working electrode 4 so that a fixed area of the working electrode 4 was exposed.

Next, a silver paste was printed on the inner surface of an electrically insulating cover 32 to form a lead 3, and then a conductive carbon paste was printed to form a counter electrode 5. Further, an insulating paste was printed to form an insulating layer 6. The cover 32 was provided with an air vent 14.

A first aqueous solution containing GOD as an enzyme and no electron mediator was dropped on the working electrode 4 of the base plate 31 and then dried to form a first reagent layer 7, while a second aqueous solution containing potassium ferricyanide as an electron mediator and no enzyme was dropped on the counter electrode 5 of the cover 32 and then dried to form a second reagent layer 8. Further, a layer 9 containing lecithin as a surface active agent was formed on the first reagent layer 7.

Finally, the base plate 31, the cover 32 and a spacer 10 were adhered to each other in a positional relationship as shown by the dashed lines of FIG. 6 to fabricate the glucose sensor.

The spacer 10 interposed between the base plate 31 and the cover 32 has a slit 11 for forming a sample solution supply pathway between the base plate 31 and the cover 32. The working electrode 4 and counter electrode 5 are positioned to face each other in the sample solution supply pathway formed in the slit 11 of the spacer 10.

Since the air vent 14 of the cover 32 communicates with this sample solution supply pathway, when a sample is brought into contact with a sample supply port 13 formed at an open end of the slit 11, the sample readily reaches the first reagent layer 7 and second reagent layer 8 in the sample solution supply pathway because of capillary phenomenon.

Next, the concentration of glucose was measured according to the same procedure as in Example 1. As a result of the measurement, a current response proportional to the concentration of glucose in the sample was observed.

In the glucose sensor of Example 3, the second reagent layer 8 contained only potassium ferricyanide, so that high linearity was observed up to a higher glucose concentration than in the glucose sensor of the comparative example, like Example 1. Also, since the working electrode 4 and the counter electrode 5 were formed at opposite positions, the current response was increased in comparison with the comparative example, like Example 2.

Moreover, since the GOD and potassium ferricyanide were separated from each other, like Example 1, the blank response was lowered and the current response was not changed so much even after a long-time storage in comparison with the comparative example.

Furthermore, since the spacer 10 was interposed between the base plate 31 and cover 32, the strength of the sensor against an external physical pressure was enhanced. As a result, the first reagent layer 7 and the second reagent layer 8 were never brought into contact with each other by the physical pressure, thereby preventing the current response from being varied by the degradation of the enzyme activity caused by the contact between GOD and potassium ferricyanide. In addition, since the volume of the sample solution supply pathway was readily kept constant, the stability of the current response was improved in comparison with Example 2.

EXAMPLE 4

In this embodiment, a glucose sensor was fabricated in the same manner as in Example 3 with the exception of the process of forming the first reagent layer 7 and second reagent layer 8.

A first aqueous solution containing GOD as an enzyme, carboxymethyl cellulose as a hydrophilic polymer and no electron mediator was dropped on the working electrode 4 of the base plate 31 and then dried to form a first reagent layer 7, while a second aqueous solution containing potassium ferricyanide as an electron mediator, carboxymethyl cellulose and no enzyme was dropped on the counter electrode 5 of the cover 32 and then dried to form a second reagent layer 8. Moreover, the layer 9 containing lecithin as a surface active agent was formed on the first reagent layer 7.

Next, the concentration of glucose was measured according to the same procedure as in Example 1. As a result of the measurement, a current response proportional to the concentration of glucose in the sample was observed.

In the glucose sensor of this example, the second reagent layer 8 contained only potassium ferricyanide, so that high linearity was observed up to a higher glucose concentration than in the glucose sensor of the comparative example, like Example 1. Also, since the working electrode 4 and the counter electrode 5 were formed at opposite positions, an increase in the response value was observed in comparison with the comparative example.

Moreover, since the GOD and potassium ferricyanide were separated from each other, the blank response was lowered and the current response was not changed so much even after a long-time storage in comparison with the comparative example.

Furthermore, since the spacer 10 was interposed between the base plate 31 and cover 32, it was possible to prevent the current response from being varied by the degradation in the enzyme activity caused by the contact between GOD and potassium ferricyanide. In addition, since the volume of the sample solution supply pathway was readily kept constant, the stability of the current response was improved in comparison with Example 2.

Besides, in comparison with Examples 2 and 3, the current response was further increased for the following reason. The presence of carboxymethyl cellulose in the first reagent layer 7 prevented adsorption of proteins to the surface of the working electrode 4, and hence the electrode reaction on the working electrode 4 proceeded smoothly. Furthermore, since the viscosity of the sample was increased during the measurement, the effects of physical impact, etc. on the sensor were reduced and variations in the sensor response were decreased.

In the above-described examples, while a voltage of 500 mV was applied to the working electrode 4 using the counter electrode 5 as reference, the voltage is not necessarily limited to 500 mV. Any voltage that enables oxidation of the electron mediator reduced with the enzyme reaction may be applied.

In the foregoing examples, the second reagent layer formed on the counter electrode contained only the electron mediator, but it may contain other components than the electron mediator as long as the inclusion of such components does not make the reaction at the counter electrode a rate determining step and the influence it may have on the blank response and storage stability is so small as to be negligible. Also, in those examples, the first reagent layer formed on the working electrode contained either only the enzyme or the enzyme and the hydrophilic polymer, but it may also contain the other components as long as the influence such inclusion may have on the blank response and storage stability is so small as to be negligible.

In the above-described examples, only one kind of electron mediator was used, but two or more kinds of electron mediators may be used.

The first reagent layer 7 and second reagent layer 8 may be immobilized on the working electrode 4 or the counter electrode 5 so as to insolubilize the enzyme or the electron mediator. In the case where the first reagent layer 7 and second reagent layer 8 are immobilized, it is preferable to use a crosslinking immobilization method or an adsorption method. Alternatively, the electron mediator and the enzyme may be mixed into the working electrode and the counter electrode, respectively.

As the surface active agent, it is possible to use a material other than lecithin. Besides, in the above-described examples, although the surface active agent layer 9 was formed only on the first reagent layer 7, or on the first reagent layer 7 and second reagent layer 8, the formation of the surface active agent layer 9 is not necessarily limited to these examples, and the surface active agent layer 9 may be formed at a position facing the sample solution supply pathway, such as a side face of the slit 11 of the spacer 10.

In the above-described examples, a two-electrode system consisting only of the working electrode and counter electrode is described. However, if a three-electrode system including an additional reference electrode is adopted, it is possible to perform a more accurate measurement.

It is preferred that the first reagent layer 7 and the second reagent layer 8 are not in contact with each other and are separated from each other with a space interposed therebetween. Accordingly, it is possible to further enhance the effect of suppressing an increase in the blank response and the effect of improving the storage stability.

As described above, according to the present invention, it is possible to obtain a biosensor having a favorable current response characteristic up to a high concentration range. Further, it is possible to obtain a biosensor having a low blank response and a high storage stability.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A biosensor comprising:
an electrode system including a working electrode and a counter electrode, for forming an electrochemical measurement system by coming in contact with a supplied sample solution;
an electrically insulating supporting member for supporting said electrode system;
a first reagent layer formed on said working electrode; and
a second reagent layer formed on said counter electrode,
wherein said first reagent layer comprises an enzyme as the main component, and said second reagent layer comprises an electron mediator as the main component, and
wherein said supporting member comprises an electrically insulating base plate and an electrically insulating cover member for forming a sample solution supply pathway or a sample solution storage section between said cover member and said base plate,
said working electrode is formed on said base plate, and
said counter electrode is formed on an inner surface of said cover member so as to face said working electrode.

2. The biosensor in accordance with claim 1, wherein the first reagent layer does not contain an electron mediator, and the second reagent layer does not contain an enzyme, and said working electrode oxidizes a reduced form of said electron mediator.

3. The biosensor in accordance with claim 1, wherein said cover member comprises a sheet member having an outwardly expanded curved section, for forming a sample solution supply pathway or a sample solution storage section between said cover member and said base plate.

4. The biosensor in accordance with claim 1, wherein said cover member comprises a spacer having a slit for forming said sample solution supply pathway and a cover for covering said spacer.

5. The biosensor in accordance with claim 1, wherein said first reagent layer contains a hydrophilic polymer.

* * * * *